(12) United States Patent
Vayser et al.

(10) Patent No.: US 9,636,182 B2
(45) Date of Patent: *May 2, 2017

(54) ILLUMINATED SUCTION APPARATUS

(75) Inventors: Alex Vayser, Mission Viejo, CA (US); Fernando Erismann, New York, NY (US); Kenneth B. Trauner, San Francisco, CA (US); Jonathan Gasson, Novato, CA (US); Derrick Richardson, Union City, CA (US)

(73) Assignee: Invuity, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/619,574

(22) Filed: Sep. 14, 2012

(65) Prior Publication Data

US 2013/0012784 A1 Jan. 10, 2013

Related U.S. Application Data (63) Continuation of application No. 12/616,095, filed on Nov. 10, 2009, now Pat. No. 8,292,805.

(51) Int. Cl.

| | | |
|---|---|---|
| *A61B 1/32* | (2006.01) | |
| *A61B 19/00* | (2006.01) | |
| *A61B 1/00* | (2006.01) | |
| *A61B 1/07* | (2006.01) | |
| *G02B 23/24* | (2006.01) | |
| *A61B 90/30* | (2016.01) | |

(Continued)

(52) U.S. Cl.
CPC ........ *A61B 19/5202* (2013.01); *A61B 1/0017* (2013.01); *A61B 1/07* (2013.01); *A61B 90/30* (2016.02); *A61M 1/008* (2013.01); *A61M 1/0041* (2013.01); *G02B 23/2469* (2013.01); *A61M 1/0047* (2013.01); *B29C 65/08* (2013.01); *B29C 65/48* (2013.01); *B29C 65/58* (2013.01); *B29C 66/71* (2013.01)

(58) Field of Classification Search
CPC . A61B 17/02–17/0293; A61B 17/3423; A61B 1/06–1/07
USPC ......... 600/177–249; 385/133, 125, 901, 902, 385/145; 362/559, 551, 562, 578
See application file for complete search history.

(56) References Cited

U.S. PATENT DOCUMENTS

| | | |
|---|---|---|
| 510,524 A | 12/1893 | Smith |
| 3,261,356 A | 7/1966 | Wallace |

(Continued)

FOREIGN PATENT DOCUMENTS

| | | |
|---|---|---|
| CN | 2045992 U | 10/1989 |
| CN | 1070739 A | 4/1993 |

(Continued)

OTHER PUBLICATIONS

International search report and written opinion dated Jul. 29, 2011 for PCT/US2010/056074.

(Continued)

*Primary Examiner* — Eduardo C Robert
*Assistant Examiner* — Michelle C Eckman
(74) *Attorney, Agent, or Firm* — Wilson Sonsini Goodrich & Rosati (57) ABSTRACT

An illuminated suction apparatus including a hand-held surgical device combining a high-performance illumination waveguide with suction. This device would be useful in a wide array of various surgical procedures including open and minimally invasive orthopedics.

40 Claims, 7 Drawing Sheets

(51) Int. Cl.

| | |
|---|---|
| A61M 1/00 | (2006.01) |
| B29C 65/08 | (2006.01) |
| B29C 65/48 | (2006.01) |
| B29C 65/58 | (2006.01) |
| B29C 65/00 | (2006.01) |

(56) References Cited

U.S. PATENT DOCUMENTS

| | | | |
|---|---|---|---|
| 3,626,471 A | 12/1971 | Florin | |
| 3,638,644 A | 2/1972 | Reick | |
| 3,641,332 A | 2/1972 | Reick et al. | |
| 3,890,960 A | 6/1975 | Wunsch et al. | |
| 4,226,228 A | 10/1980 | Shin et al. | |
| 4,416,268 A | 11/1983 | Hagino | |
| 4,562,832 A | 1/1986 | Wilder et al. | |
| 4,592,344 A | 6/1986 | Scheer | |
| 4,597,030 A | 6/1986 | Brody et al. | |
| 4,605,990 A | 8/1986 | Wilder et al. | |
| 4,643,172 A | 2/1987 | Taff et al. | |
| 4,697,578 A | 10/1987 | Burgin | |
| 4,807,599 A | 2/1989 | Robinson et al. | |
| 4,842,356 A | 6/1989 | Mori | |
| 4,872,837 A | 10/1989 | Issalene et al. | |
| 4,961,617 A | 10/1990 | Shahidi et al. | |
| 4,992,047 A | 2/1991 | Warner | |
| 5,035,232 A | 7/1991 | Lutze et al. | |
| 5,046,482 A | 9/1991 | Everest | |
| 5,052,778 A * | 10/1991 | Jamshid | B29C 47/0016 385/123 |
| 5,213,092 A | 5/1993 | Uram | |
| 5,281,134 A * | 1/1994 | Schultz | 433/29 |
| 5,353,786 A | 10/1994 | Wilk et al. | |
| 5,478,338 A * | 12/1995 | Reynard | 606/15 |
| 5,536,265 A | 7/1996 | van den Bergh et al. | |
| 5,588,952 A | 12/1996 | Dandolu | |
| 5,645,519 A | 7/1997 | Lee et al. | |
| 5,651,783 A | 7/1997 | Reynard | |
| 5,815,627 A | 9/1998 | Harrington | |
| 5,931,670 A | 8/1999 | davis | |
| 6,115,523 A | 9/2000 | Choi et al. | |
| 6,135,947 A * | 10/2000 | Watanabe et al. | 600/178 |
| 6,185,356 B1 * | 2/2001 | Parker et al. | 385/133 |
| 6,406,293 B1 | 6/2002 | Burstein | |
| 6,504,985 B2 | 1/2003 | Parker et al. | |
| 6,508,758 B2 * | 1/2003 | Komi | 600/131 |
| 7,226,413 B2 * | 6/2007 | McKinley | 600/210 |
| 7,306,559 B2 * | 12/2007 | Williams | 600/245 |
| 7,620,279 B2 | 11/2009 | Joseph | |
| 7,842,027 B2 | 11/2010 | Lieponis | |
| 7,901,353 B2 * | 3/2011 | Vayser et al. | 600/182 |
| 8,142,352 B2 * | 3/2012 | Vivenzio et al. | 600/199 |
| 8,292,805 B2 * | 10/2012 | Vayser et al. | 600/249 |
| 8,317,693 B2 * | 11/2012 | Grey et al. | 600/212 |
| 8,936,551 B2 | 1/2015 | Vayser et al. | |
| 2002/0001202 A1 * | 1/2002 | Williams et al. | 362/572 |
| 2002/0013574 A1 * | 1/2002 | Elbrecht et al. | 606/5 |
| 2003/0044144 A1 | 3/2003 | Nelson et al. | |
| 2003/0044149 A1 | 3/2003 | Fraval et al. | |
| 2003/0095781 A1 | 5/2003 | Williams | |
| 2004/0143164 A1 * | 7/2004 | Suddaby | A61B 17/0218 600/210 |
| 2005/0171408 A1 * | 8/2005 | Parker | 600/249 |
| 2005/0213903 A1 | 9/2005 | Mohler et al. | |
| 2005/0279354 A1 * | 12/2005 | Deutsch | A61B 1/07 128/200.24 |
| 2006/0069386 A1 | 3/2006 | Dubnack et al. | |
| 2006/0211918 A1 | 9/2006 | Lieponis | |
| 2006/0217596 A1 * | 9/2006 | Williams | 600/245 |
| 2006/0241351 A1 | 10/2006 | Feng et al. | |
| 2006/0268570 A1 * | 11/2006 | Vayser et al. | 362/572 |
| 2007/0024971 A1 | 2/2007 | Cassarly et al. | |
| 2007/0179430 A1 * | 8/2007 | Smith | A61B 17/3421 604/20 |
| 2007/0208226 A1 * | 9/2007 | Grey et al. | 600/212 |
| 2007/0270653 A1 * | 11/2007 | Vayser | A61B 1/00135 600/182 |
| 2007/0293726 A1 * | 12/2007 | Goldfarb et al. | 600/178 |
| 2007/0293727 A1 * | 12/2007 | Goldfarb et al. | 600/178 |
| 2008/0269735 A1 | 10/2008 | Vila Echague et al. | |
| 2009/0018531 A1 * | 1/2009 | Welches et al. | 606/2 |
| 2009/0036744 A1 * | 2/2009 | Vayser | 600/182 |
| 2009/0221991 A1 | 9/2009 | Lieponis | |
| 2010/0016844 A1 | 1/2010 | Patel, Jr. | |
| 2010/0041955 A1 * | 2/2010 | Grey et al. | 600/212 |
| 2010/0135626 A1 | 6/2010 | Sun et al. | |
| 2010/0196207 A1 * | 8/2010 | Steinmiller | B01L 3/502707 422/82.09 |
| 2010/0329693 A1 | 12/2010 | Chen | |
| 2011/0112376 A1 * | 5/2011 | Vayser et al. | 600/249 |
| 2011/0172519 A1 | 7/2011 | Cao et al. | |
| 2011/0230722 A1 | 9/2011 | Kudo et al. | |
| 2012/0041268 A1 | 2/2012 | Grey et al. | |
| 2012/0203075 A1 | 8/2012 | Horvath et al. | |
| 2012/0209074 A1 * | 8/2012 | Titus | 600/153 |
| 2012/0265094 A1 * | 10/2012 | Goldfarb et al. | 600/562 |
| 2012/0330107 A1 * | 12/2012 | Vayser et al. | 600/249 |
| 2013/0012783 A1 * | 1/2013 | Vayser et al. | 600/249 |
| 2013/0079598 A1 * | 3/2013 | Auld et al. | 600/249 |
| 2013/0245756 A1 | 9/2013 | Liao | |
| 2013/0267664 A1 | 10/2013 | Vayser et al. | |
| 2013/0289956 A1 | 10/2013 | Tudury et al. | |
| 2014/0043856 A1 | 2/2014 | Thompson et al. | |
| 2014/0046141 A1 | 2/2014 | Vayser et al. | |
| 2014/0088371 A1 | 3/2014 | Vayser et al. | |
| 2014/0303446 A1 | 10/2014 | Michler et al. | |
| 2014/0341521 A1 | 11/2014 | Fabian et al. | |
| 2015/0011837 A1 | 1/2015 | Johnson et al. | |
| 2015/0018627 A1 | 1/2015 | Vayser et al. | |
| 2015/0093080 A1 | 4/2015 | Derosa et al. | |

FOREIGN PATENT DOCUMENTS

| | | |
|---|---|---|
| CN | 1505771 A | 6/2004 |
| CN | 2698355 Y | 5/2005 |
| EP | 0101781 A1 | 3/1984 |
| GB | 2078526 A | 1/1982 |
| JP | 2002-186578 A | 7/2002 |
| JP | 2007-117114 A | 5/2007 |
| WO | WO 01/37739 A1 | 5/2001 |

OTHER PUBLICATIONS

European search report and opinion dated Mar. 18, 2013 for EP Application No. 10830601.0.
Office Action dated Feb. 8, 2012 for U.S. Appl. No. 12/616,095.
U.S. Appl. No. 14/057,933, filed Oct. 18, 2013, Vayser et al.
Notice of allowance dated Jun. 12, 2012 for U.S. Appl. No. 12/616,095.
Office action dated Jun. 15, 2015 for U.S. Appl. No. 14/057,933.
Office action dated Feb. 3, 2016 for U.S. Appl. No. 14/057,933.
Office action dated Dec. 1, 2016 for U.S. Appl. No. 14/057,933.

* cited by examiner

ILLUMINATED SUCTION APPARATUS

RELATED APPLICATIONS

The present application is a continuation of U.S. patent application Ser. No. 12/616,095 filed on Nov. 10, 2009; the entire contents of which are incorporated herein by reference.

FIELD OF THE INVENTIONS

The present invention relates generally to the field of surgical illumination and more specifically to illumination systems with integrated surgical tools.

BACKGROUND OF THE INVENTIONS

In various surgical procedures, illumination of the surgical field is typically achieved through the use of headlamps and surgical microscopes. There are scenarios in which these illumination sources provide lighting that is either poor in quality or poorly directed. As an example, during spinal surgery from the lumbar approach, access to the desired anatomical target area may be achieved through an angled incision on one side of the patient's midline. Light emanating from an operating microscope is static and may be poorly directed relative to the angle of surgical access. Conversely, light from a headlamp may be adjusted as a physician tilts or moves his head to redirect the output beam, but still may be blocked by various anatomical structures such as the spinous process or layers of tissue and muscle. Lighting from either source may not be adequate as the physician progresses through various phases of the procedure requiring visualization of the anatomy at varied depths from the skin-level incision.

Hand-held suction devices are routinely used during surgical procedures such as spine surgery. These devices are typically connected to a standard suction source in the operating room, enabling the physician to dynamically and efficiently remove blood, bone fragments, or fluid previously irrigated into the surgical site. These suction devices are sometimes also used to provide low force retraction of fat, muscle, or other structures during the procedure. The surgeon holds the suction device from its proximal end, manipulating the distal portion of the suction device during the surgical procedure in order to provide suction at the desired location. Hand-held suction devices are widely available in a variety of distal tip configurations suited to various surgical applications (Frazier, Poole, Fukijima, etc).

Conventional suction devices have been constructed with fiber optic cable encased in metallic tubing and connected to metallic suction devices to provide some level of illumination. These devices face multiple challenges. These devices have traditionally been manufactured with narrow fiber optic assemblies of 2.5 mm or less in diameter. These assemblies, with limited cross section, are only capable of transmitting less than 50% of the output light from a standard 5 mm fiber optic cable attached to standard light sources in the operating room. Inefficiencies in the fiber-to-fiber coupling with high intensity light leads to light losses at the interface which produces heat. Losses are caused by non-transmissive zones between the optical fibers and Fresnel reflections at the interface. The spatial zones between the fibers are frequently the dominant cause of light loss and heat. Excess heat at the interface can cause thermal damage to the tissues and is also a fire hazard in the operating room. Due to the fiber/fiber interface concerns, some manufacturers have produced more expensive devices in which the connection is eliminated and the entire fiber optic bundle acts as the surgical light source. Other manufacturers recommend limiting the amount of light that can be transmitted to the operative device and interface.

SUMMARY

The devices described below provide improved illumination in a surgical suction device. The illuminated suction device described below includes a metal suction tube having a proximal end and a distal end connected by a central portion. The proximal end of the suction tube is provided with fittings for connection to a vacuum source. The suction tube has an inner surface and an outer surface, with a layer of optical cladding having a refractive index between 1.29 and 1.67 on the outer surface of the central section of the suction tube, and a illumination waveguide having a proximal end and a distal end. The illumination waveguide is formed surrounding the optical cladding on the central portion of the suction tube, and serves to conduct light around the suction tube from the proximal end to the distal end of the illumination waveguide. The illumination waveguide has a refractive index between 1.46 and 1.7 and a numerical aperture between 0.33 and 0.70. An illumination input is formed into the proximal end of the illumination waveguide for conducting light from a source to the illumination waveguide.

The illuminated suction apparatus includes suction and illumination functions integrated into a hand-held device suited to meet the ergonomic needs of the physician. The hand-held, repositionable suction function already prevalently used in surgical procedures is surrounded by an illuminated waveguide which enables the physician to apply lighting directly to the desired region of the anatomy below the skin regardless of incision angle, depth, and surrounding anatomical obstructions. The illumination waveguide is a solid structure designed to specifically guide light from a high-intensity light source and is fabricated using an optical-grade polymer with a specific index of refraction such as cyclo-olefin polymer or copolymer or any other suitable acrylic or plastic. Furthermore, the illumination waveguide can be engineered to efficiently transmit light from its distal output by sheathing or surrounding it with a second material of lower index of refraction properly coordinated to the index of refraction of the core material to preserve Total Internal Reflection (TIR). This solid-state, structure guided illumination waveguide is powered via a fiber optic cable connected to a high intensity light source such as 300 W xenon sources supplied by Luxtec, BFW, and others.

The illuminated suction apparatus may also include one or more barbs, ridges or other protrusions on the proximal end of the suction lumen enabling the connection of standard PVC surgical tubing or other suitable vacuum conduit.

The use of a generally solid waveguide for suction illumination, rather than optical fibers, eliminates losses due to the non-transmissive spaces between the optical fibers and reduces losses solely to those associated with Fresnel reflections. The marked reduction in losses associated with a fiber/fiber junction allows for high intensity light transmission to the waveguide without significant heating of the interface or need for heat sink devices or mechanisms at the interface. With a fiber to waveguide connection, light from a standard 300 watt light source can be transmitted with use of standard connectors such as ACMI, with a steady state temperature below the temperatures harmful to body tissue without design alteration.

Use of total internal reflection and light mixing in an illumination waveguide enables control of the output light profile and enables custom illumination profiles. Microstructures can be applied to any suitable surfaces of the illumination waveguide and light can be extracted incrementally along the walls of the device with injection molded structures and other suitable structures at minimal added cost. Use of sequential extraction surfaces, changes in the numerical aperture of the device as a function of position, use of extraction structures—either micro or macro structural, with or without changes in the numerical aperture, selective cladding, selective reflective coatings, etc, all can be used to shape the output profile of the waveguide to meet the design specifications or light specifications requested by the user for specific surgical suction illumination applications.

The device is meant to be disposable, fabricated out of low cost materials to enable leverage of manufacturing efficiencies through use of processes such as high-volume injection molding, over-molding, and metal & polymer extrusion. Device assembly would be engineered to minimize labor costs. A low cost, high-performance combination device provides an attractive alternative to existing discrete illumination and suction devices while minimizing incremental cost to the user.

The illuminated suction apparatus comprises a hand-held surgical device combining a high-performance illumination waveguide with suction. This device would be useful in various surgical procedures including open and minimally invasive orthopedics. The illumination waveguide may also be combined with other surgical devices such as surgical drills and probes, etc.

The surgical suction field must be illuminated by the illumination waveguide while the distal suction tip is in active contact with the tissue and or fluid surface. To achieve this effect, the output light from the illumination waveguide must emanate from a point on the waveguide that is proximal to the distal suction tip of the device. In surgery, when using a suction illumination device in which the output light emanates from a point proximal to the distal end of the device, a surgeon may experience difficulty. When focused on the surgical field, the surgeon uses his/her peripheral vision to watch the suction device being used in the periphery. In spine surgery, the suction device frequently is used as a retractor while the surgeon works in the vicinity of the spinal cord. The problem is that while focused on the surgical field the surgeon uses the central portion of the visual field produced by rods for the high acuity work, the brain misinterprets the location of the light source in the periphery of the visual field as the location of the distal tip of the suction device. The surgeon may be inclined to plunge the device deeper within the wound. For safety, the surgeon must frequently shift his eyes from the surgical field to check on the position of the suction tip.

In an alternate configuration, the distal tip of the suction tube may be configured to transmit light or reflect light such that the surgeon sees the distal tip of the suction as illuminated such that he/she can localize the distal tip of the suction device in their peripheral vision without directly looking at or focusing on the tip of the device. Extending a thin layer of the waveguide to the tip can provide the effect. Strategies that implement this effect include but are not limited to: (a) waveguide extended to the tip with or without surface extraction features to cause light to back reflect or scatter off the tip, (b) Use of a thin layer of optically transmissive material with high scattering coefficient to cause the suction device to glow (c) reflective surfaces applied to the outside of the central suction device (d) reflective surfaces applied with imperfections on the surface to reflect or scatter the light off the outer surface (e) use of a cladding material applied to the walls of the inner suction tube that transmits or scatters a portion of the output light, the input to the cladding being either an imperfection in the cladding or naturally occurring leakage, (f) fluorescent coating on the tip, (g) phosphorescent coatings (h) use of embedded or graded reflectors along or at the tip of the device. Alternatively, the distal tip geometry could be formed to intentionally scatter light (square edges, etc).

One or more surfaces in an optical waveguide sheath or adapters or connectors may be polarized using any suitable technique such as micro-optic structure, thin film coating or other. Use of polarized light in a surgical environment may provide superior illumination and coupled with the use of complementary polarized coatings on viewing devices such as cameras or surgeon's glasses may reduce reflected glare providing less visual distortion and more accurate color rendering of the surgical site. One or more surfaces of an optical waveguide sheath may also include light filtering elements to emit light of one or more frequencies that may enhance visualization of specific tissues.

DETAILED DESCRIPTION OF THE INVENTIONS

Figure 1:
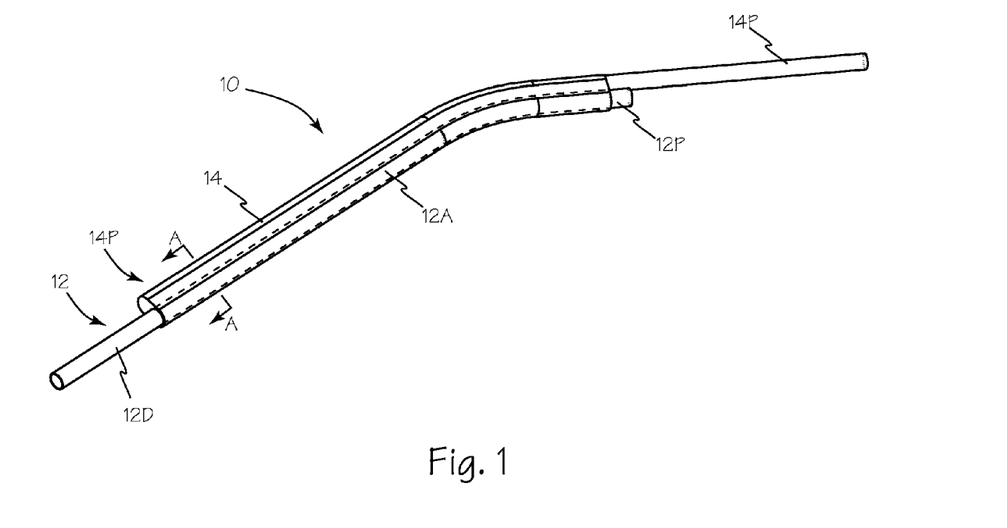
FIG. 1 is a perspective view of an illuminated suction apparatus.
Figure 2:
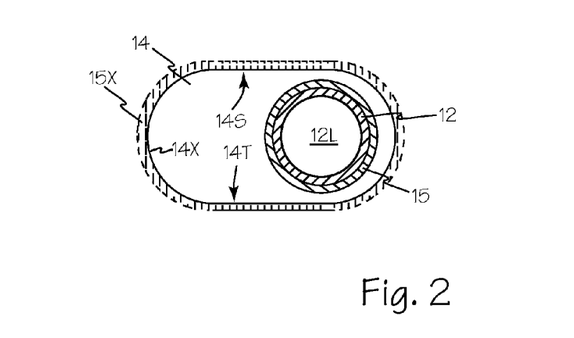
FIG. 2 is a cross-section view of the illuminated suction apparatus of FIG. 1 taken along A-A.

Referring to FIGS. 1 and 2, illuminated suction apparatus 10 includes suction tube 12 made of any suitable material such as aluminum, stainless steel or any suitable acrylic or other polymer. Suction tube 12 encloses suction lumen 12L. Illumination waveguide 14 is secured over cladding layer 15 on central portion 12A of suction tube 12 leaving input or proximal portion 12P and distal portion 12D exposed. Illumination waveguide 14 may have a flat side such as side 14S or side 14T to optimize light mixing as light 11L travels from illuminator input 14P to output 14D.

Illumination waveguide 14 is made of an optical grade engineering thermoplastic such as cyclo olefin polymer which efficiently transmits light. Any other suitable material such as Cyclic Olefin Copolymer, Polycarbonate, Acrylic and or TPC may also be used. The angles and bends of the waveguide structure are engineered so light transmits through the waveguide via TIR. The side walls and other features have angles and flat areas such that light is mixed and not allowed to escape until it reaches the distal end of the illuminator and exits with a selected uniformity. Light that is reflected by TIR is reflected with high efficiency (nearly 100% efficiency). Suction tube 12 introduces an interface with illumination waveguide 14 that will not be 100% reflective. Thus an uncoated or untreated suction tube will cause a small portion of light to be lost to absorption and or scattering at each reflection, ultimately resulting in poor light transmission efficiency. In order to preserve TIR through the waveguide, cladding material 15 with a specific index is placed between the suction tube and the waveguide. TIR can also be potentially disrupted by blood or foreign matter from the surgical site coming into contact with exterior exposed surface 14X of illumination waveguide 14. Exterior cladding layer 15X having a specific refractive index can also be attached to the outside of the waveguide. The waveguide material completely surrounds suction tube 12 in order to provide an illumination pattern from distal end 14D unobstructed by a shadow from the metallic suction tube. The waveguide and TIR-preserving materials are chosen to provide an optimized light exit angle, total light output, and illumination suited to properly visualize the surgical site. Suction tube 12 could be treated (for example anodized in the case of aluminum) in order to reduce glare or reflections resulting from interaction with light output from the illuminator.

Figure 3:
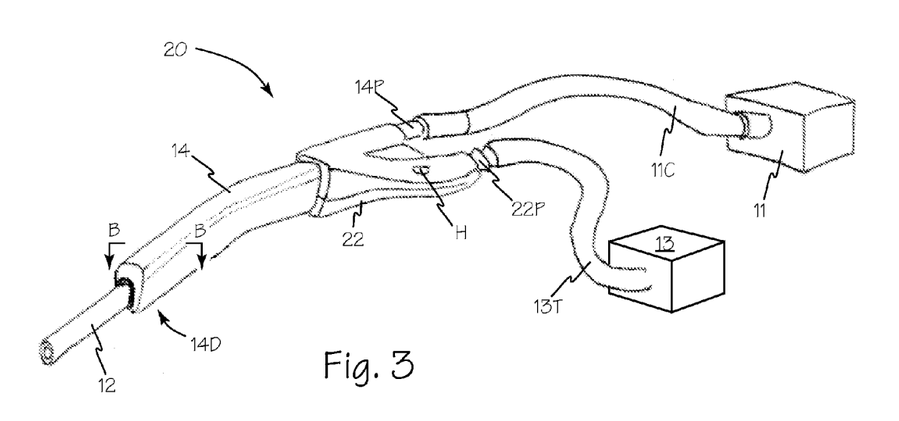
FIG. 3 is a perspective view of an illuminated suction apparatus with a handle.

Referring now to FIG. 3, Light 11L from light source 11 is conducted to the illumination waveguide using any suitable apparatus such as fiber optic cable 11C and is then conducted through waveguide 14 and exits from any appropriate structure or structures on or near distal end 14D of the waveguide. Vacuum from suction source 13 is conducted to illuminated suction apparatus 19 using any suitable suction tube such as tube 13T which is connected to vacuum input 21P. The vacuum available at the distal end of suction tube 12 may be controlled by covering all or a portion of suction hole H in handle 21.

Illuminated suction apparatus 10 may be integrated into a handle such as handle 21 made of relatively low-cost engineering plastic such as ABS or polycarbonate. Handle 21 may be formed from two or more components that could be separate injection molded components designed to be snap fit, glued, or ultrasonically welded together. Alternatively, the handle could be formed over an illuminated suction apparatus such as apparatus 10 through an overmolding process. The proximal portion of the combined device such as illuminated suction apparatus 19 would also contain a hole, hole H, properly positioned to allow the surgeon to enable the suction function by obstructing all or a portion of the hole with a finger; the hole communicates with the suction pathway in the device, disabling suction by creating a "suction leak" when it is not blocked. Varying the hole geometry, as in the case of Fukijima suction, affords finer modulation of the suction function. The proximal end of handle 21 may also contain inputs for a traditional fiber optic cable to be attached to illumination waveguide 14, such as a male ACMI connection or other suitable connector, and a vacuum port such as vacuum port 21P which may be a barbed fitting suitable for standard flexible suction PVC suction tubing of various sizes to be attached. The fiber optic cable is attached to a high-intensity light source such as light 11. Suction tube 13T is attached to any standard vacuum source in the OR such as a waste collection container with integrated vacuum pump such as vacuum source 13.

Figure 4:
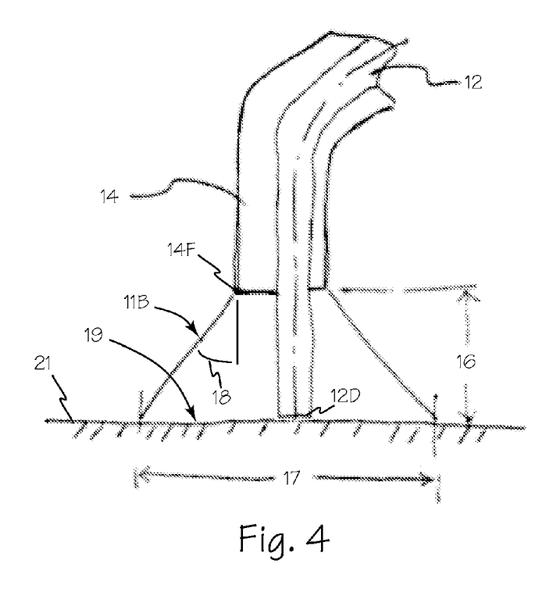
FIG. 4 is a cross section view of the distal end of the illuminated suction apparatus of FIG. 3 taken along B-B.

Referring now to FIG. 4, light beam 11B exits waveguide distal face 14F at a specific angle based on the optical properties such as the numerical aperture (NA) of the input source, index of refraction of the material, and shape of the waveguide. Light pattern cast onto the target surgical field is optimized based on the specific distance 16 the illuminator is set back from the distal tip 12D of the suction tube. For a given light source configuration, divergence angle 18 of light beam 11B results in a specific illumination pattern 19 with a total light output and illumination size 17 at any target plane normal to the illuminator such as plane 21. The plane at the distal tip of the suction tube is of particular interest, since the physician will place the distal tip at the desired surgical target to enable suction or retract tissue.

Figure 5:
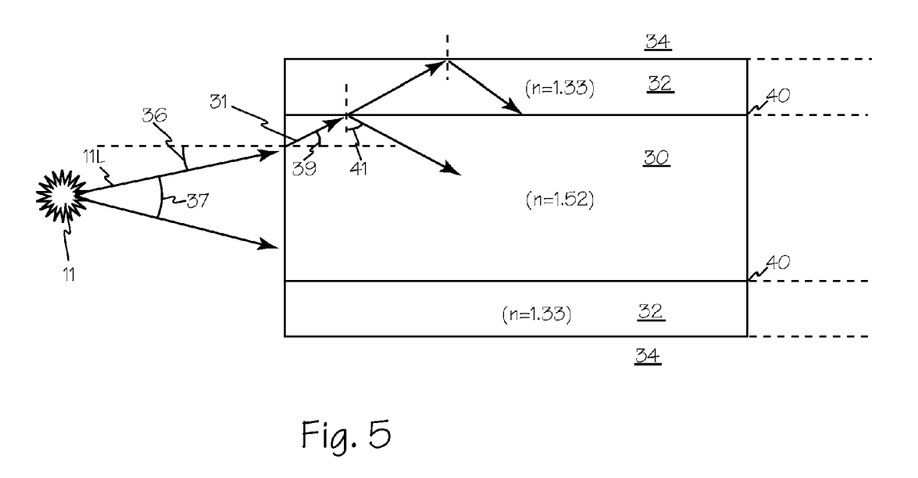
FIG. 5 is a cross section view of an illumination conduit input according to the present disclosure.

Referring now to FIG. 5, light source 11 is transmitting light 11L into cyclo olefin polymer core 30 with refractive index 1.52, fluorinated ethylene propylene (FEP) cladding 32 with refractive index 1.33, and an external environment 34 surrounding cladding 32. Light source 11 is assumed to be in air with a refractive index of 1 and a numerical aperture (NA) of 0.55 which corresponds to a half-cone angle, angle 36, of 33.4 degrees. The NA of source 11 is the angle of incidence on the core when light 11L is coupled in which corresponds to angle 37. Internal light rays 31 initially enter core 30 at the half cone angle of 33.4 degrees and are refracted at an angle of 21.2 degrees, internal refraction angle 39 when they pass into core 30. Internal light 31 then intersects core-cladding boundary 40 at an angle of 68.8 degrees which is angle 41. As long as angle 40 is greater than the critical angle determined by the core and cladding indexes, light 31 will undergo TIR and none of light 31 will be transmitted into the cladding. In this case (n-core=1.52 & n-cladding=1.33) the critical angle is 61.0 degrees.

This ray trace can be worked backwards from the critical angle to determine the maximum source NA that will still allow for all light to undergo TIR at the core-cladding boundary. If reflection angle 41 is 61.0 degrees which corresponds to the critical angle for the selected core and cladding, then internal refraction angle 39 is 29 degrees which means that angle 37 must be 47.4 degrees. From 47.4 degrees, the source NA is calculated to be 0.74. Therefore, when using the cyclo olefin polymer/FEP combination, an input source with a much higher NA/Efficiency can be used.

If the source NA is such that all the light coupled into the waveguide undergoes TIR at the core-cladding boundary, then no light is propagating in the cladding and the environment index does not affect the waveguide transmission and no light is hitting the cladding-environment boundary. The data in the following table shows how the critical angle changes at the core-cladding boundary as the cladding index changes from 1.0 to 1.46 for a cyclo olefin polymer core (n=1.52). This is particularly relevant when designing refractive structures. Knowing the critical angle ahead of time, based on the environment or cladding, the structures can be designed to preferentially leak light from the illumination conduit.

| Cladding Index | Core-Cladding Critical Angle (degrees) |
|---|---|
| 1.00 | 41.1 |
| 1.10 | 46.4 |
| 1.20 | 52.1 |
| 1.30 | 58.8 |
| 1.40 | 67.1 |
| 1.417 | 68.8 |
| 1.42 | 69.1 |
| 1.44 | 71.3 |
| 1.46 | 73.8 |

When using FEP as a cladding with cyclo olefin polymer, the critical angle is smaller than the angle from the 0.55NA (68.8 degrees). If no cladding is used, at the index of 1.417 and higher, the critical angle equals to the input angle causing light leakage because TIR is not maintained. Moreover, the combination of a cyclo olefin polymer core with FEP cladding allows the use of an input source with NA exceeding 0.55. The input source would enable greater light capture from a source due to the larger acceptance angle and provide more light through the illumination conduit assuming constant transmission efficiency. Understanding the critical angles of FEP and open environment, structures can be designed more accurately to extract the light from the illumination conduit.

Any suitable cladding materials such as FEP can be applied to central portion 12A of suction tube 12 thorough methods such as manual or semi-automated shrink-application of oversized FEP with a heat gun or focused heat from a hot-box nozzle, leveraging FEP's characteristic shrink ratio. Any other technique of a cladding such as FEP may be used such as applying a liquid coating of FEP to central portion 12A or any other suitable surface to be clad. Suction tube 12 with integrated cladding 15 can then have illumination waveguide 14 insert-molded (via conventional high-volume injection molding) and waveguide 14 will able to maintain total internal reflection. Use of cladding 15 between suction tube 12 and illumination waveguide 14 enables the suction tube to be formed of any suitable material such as metal or plastic. The choice of the plastic material for the suction tube needs to be such that the index of that material is below 1.42 for use with a waveguide having an index of 1.52 to maintain the differential at the interface of the suction tube and the waveguide. However, use of plastic may create challenges with injection molding processes which require relatively high temperatures and pressures inside of the molding cavity. Alternatively the device can be manufactured such that illumination waveguide 14 is formed with an internal lumen with no additional suction conduit running through it. The challenge posed by this approach is the potential light transmission efficiency losses stemming from evacuating biological material (blood, etc) through the lumen and making contact with the internal surface of the illumination waveguide lumen throughout the procedure.

Cladding with an index of 1.33 shows no light transmission dependence on the environmental index or the cladding thickness when used with an illumination waveguide having a refractive index at or near 1.52. For a cladding with an index of 1.33, the light coupled into the illumination waveguide is constrained to the core due to total internal reflection at the core-cladding interface. Thus, there is no light propagating through the cladding, making the cladding-environment boundary condition a negligible factor in transmission. Teflon FEP with an index of 1.33 used as a cladding material with a cyclo olefin polymer core with index 1.52, shows no dependence on cladding thickness in three representative simulated surgical environments. Therefore there is no constraint on the cladding thickness of FEP when used with material similar to cyclo olefin polymer.

An illumination waveguide formed from material with a refractive index of 1.46, showed light transmission dependence on both cladding thickness as well as the external environment. This is a result of introducing light into the illumination waveguide at an NA of 0.55. Under this condition, light enters the core at an angle that is less than the critical angle of the core-cladding boundary, resulting in light propagating into the cladding. Since light propagates through the cladding, the cladding-environment boundary condition (critical angle) is a factor in the light transmission. Due to light propagating through the cladding, the cladding thickness also affects the transmission, because as the thickness increases, the rays bounce at the boundaries fewer times as they traverse the length of the waveguide.

Straight waveguide geometry in which the light traversing the structure encounters no bends or radii results in the greatest optical efficiency. However, due to ergonomic constraints or compatibility & management of essential accessories related to the device such as proximally attached fiber optic cables and suction tubing, it may be advantageous to design the proximal light input such that it creates an angle relative to the distal transmission body of the waveguide structure.

Figures 6, 6A:
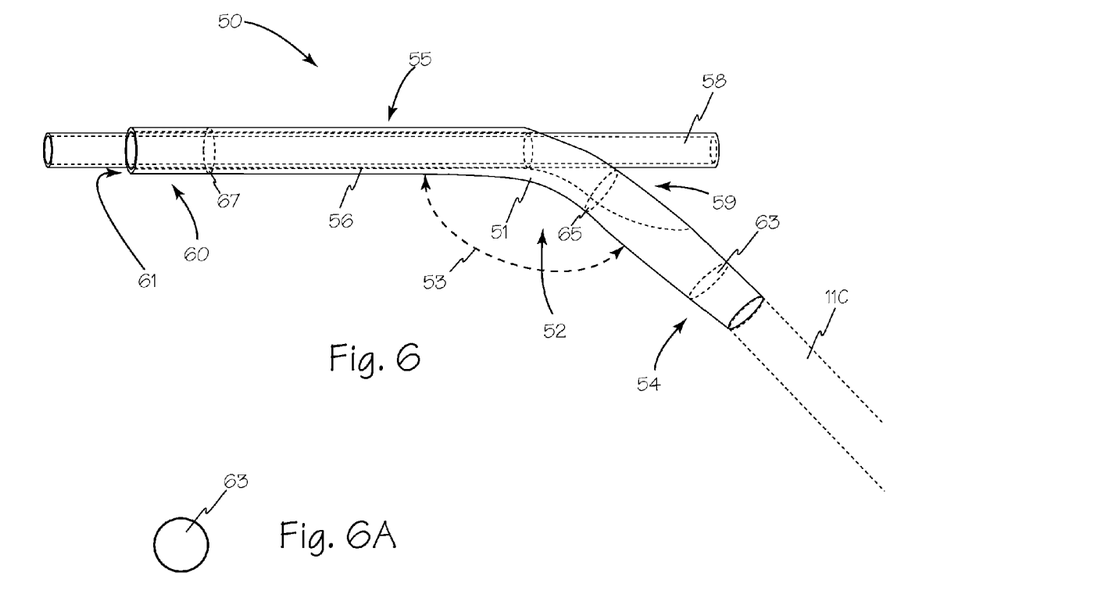
FIG. 6 is a side view of an alternate illumination conduit.
FIGS. 6A, 6B and 6C are various cross-section views of the alternate illumination conduit of FIG. 6.
Figure 6B:
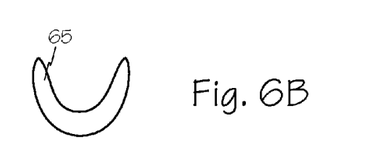
Figure 6C:
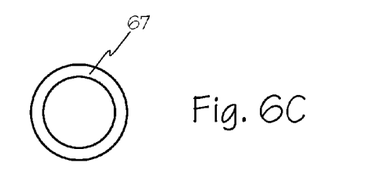

Referring now to FIGS. 6 and 6A, To preserve TIR and maximize transmission efficiency in illuminated waveguide 51 of suction apparatus 50, central portion 52 between light input section 54 and illuminated waveguide body 55 should be curved to form angle 53 between the input and body as close to 180 degrees as possible. Almost any bend or radius in the tube will cause some light leakage. However, if angle 53 in central portion 52 is limited to 150 degrees or greater, the light leakage is very low and the light transmission efficiency is maximized.

Figure 6D:
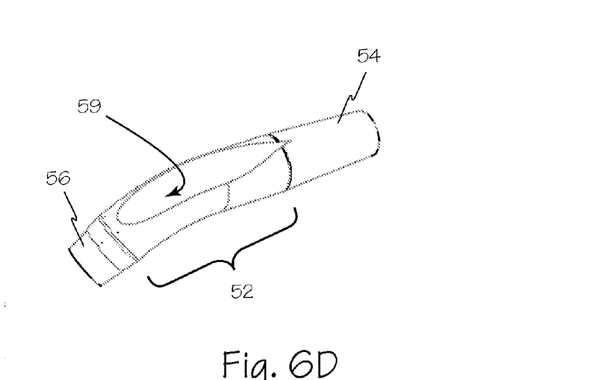
FIG. 6D is a perspective view of access port of the alternate illumination conduit of FIG. 6.

The shape of illuminated waveguide 51 morphs or cylindrically "sweeps" or "blends" from a solid cylindrical input, input section 54 into a circular hollow tube of waveguide body 55. Waveguide bore 56 may accommodate any suitable surgical tools such as suction tube 58. Suitable surgical tools access waveguide bore 56 through access opening 59. As discussed above, light exits waveguide body at or near distal end 60 with the majority of light exiting through distal surface 61.

As the cross sectional area of illuminated waveguide 51 increases along the light transmission path from section 63 of input section 54 to central section 65, to distal cross-section 67 near distal end 60, the NA of the illumination waveguide increases, thus increasing the light divergence as light emerges from the distal end of the illuminator. The NA can also be influenced by bends. It may be possible to counter-bend to adjust the NA. The concepts illustrated above can also be manufactured as two halves that are over molded around any suitable surgical tool such as suction tube 58.

Figure 7:
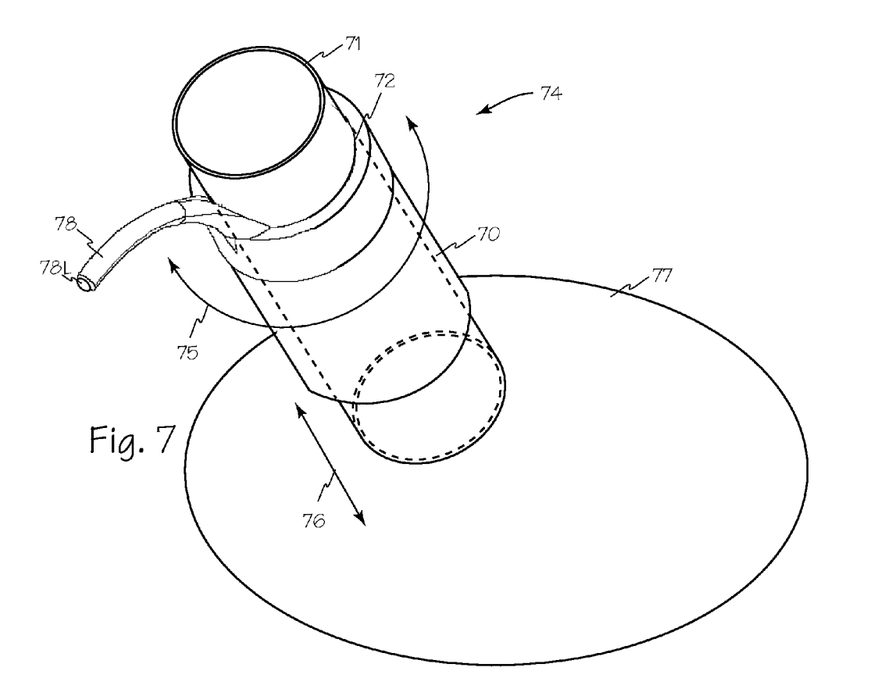
FIG. 7 is perspective view of the illumination input of an alternate illumination conduit.

Referring now to FIG. 7, disposable illuminated waveguide 70 can be supplied as a stand-alone device. Various suction devices or other suitable tools such as suction tool 71 can be inserted though central bore 72, the working channel of the illumination waveguide. A connection could be constructed between waveguide 70 and a surgical tool such as suction tool 71 that would allow the waveguide to be secured to various suction devices, enabling both waveguide 70 and suction tool 71 to be manipulated as a single unit. This concept can be applied to other devices that would fit through central bore 72 such as drills, etc. Additionally, illuminated surgical apparatus 74 lends itself to dynamic positioning of the waveguide 70 relative to any surgical tool inserted in central bore 72, such as suction tool 71. For example, the user could rotate the illuminator about the suction device as in rotation 75, as well as telescope illuminator along the length of the suction tube along path 76, repositioning or expanding or contracting illumination field 77 as needed during the procedure.

Figure 8:
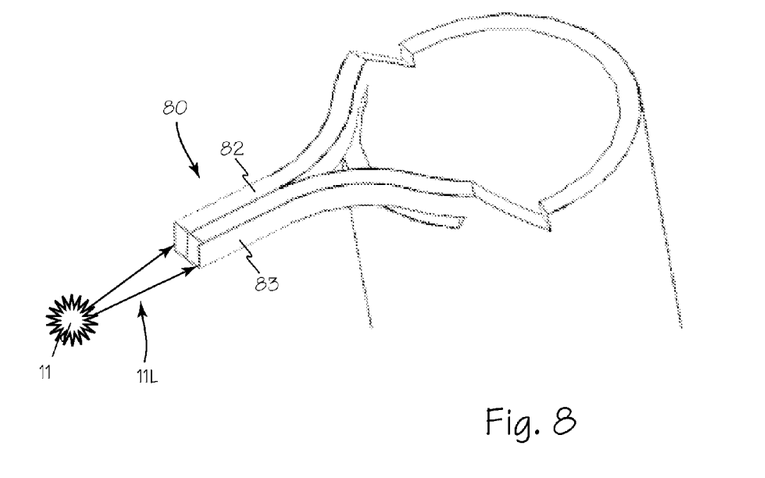
FIG. 8 is perspective view of the illumination input of another alternate illumination conduit.

An alternative approach involves splitting the solid input circle or ellipse such as input 78 of FIG. 7 and split input 80 is formed as in FIG. 8 in which half of input light 11L is directed to one half of the input, arm 82, and the other half of input light 11L is directed to the second half of the input, arm 83. Here, arms 82 and 83 come together in a generally rectangular cross-section as input 80 to engage fiber optic cable 11C. However, input 80 can have circular cross-section with semi-circular arm(s), elliptical or multi faceted for better mixing of light. The configuration could also have FEP cladding strategically applied to one or more areas of each arm to preserve TIR. To enable proper function of the light extraction features, holes, or other suitable shapes could be cut into the FEP or other cladding, enabling a desired balance of TIR preservation and suitable light leakage from specific zones of the device.

Additional microstructure features can be added to the distal end of an illumination waveguide to optimize control of the illumination pattern as well as to homogenize the light output field. Anti-reflection features, typically diffractive in nature and sub-micron in size, can be added to the input and output faces of the illuminator to reduce normal Fresnel reflection losses. The features of the waveguide, such as curves, bends, and mounting features, can cause undesired reflections, light leakage, glare, and non-uniform output patterns resulting in poor performance. Adding microstructure features which may be refractive or diffractive on or near the distal portion of the illumination waveguide can potentially provide better light uniformity and or to bias the divergence or convergence of the illumination pattern as well to homogenize the light output of the illumination field. Features or tapering of the waveguide can also be added to the outside of an illumination waveguide to control the illumination output. Furthermore, micro lenses such as lens 78L or other micropattern structures can be added to an illumination waveguide input such as input 78 to better control the input beam shape or other light input characteristics. The light input arm can be round, square or multi faceted to provide a better mix of the light.

The waveguide can be made in various shapes or cross sections. Currently preferred cross-sectional shapes are round, elliptical, or hexagonal. Other cross-sectional shapes such as rectangles, triangles, or squares are possible. However, generally regular surfaces of the waveguide, as well as odd number of surfaces may cause a secondary pattern at the output. This pattern would manifest as bright and dark spots. Cross sections resembling even numbered higher order polygons such as the hexagon are currently preferred. As the number of faces in the cross-section increase, these cross sections would approach a circle, such a device design would potentially complicate manufacturing processing (such as injection molding), thereby increasing costs.

The illuminator can be tapered to increase or decrease its cross section as light travels from the input to extraction zones. Tapering biases the NA, causing either a tighter output spot (for increased area at the exit) or a larger more diffuse spot (decreased exit surface area, breaking TIR).

For an illuminated suction device, in many surgical applications, there is a need for circumferential illumination around the device. The illumination may need to be uniformly circumferential or delivered in an off axis orientation for most of the lighting to orient anterior to the retractor.

Figure 9:
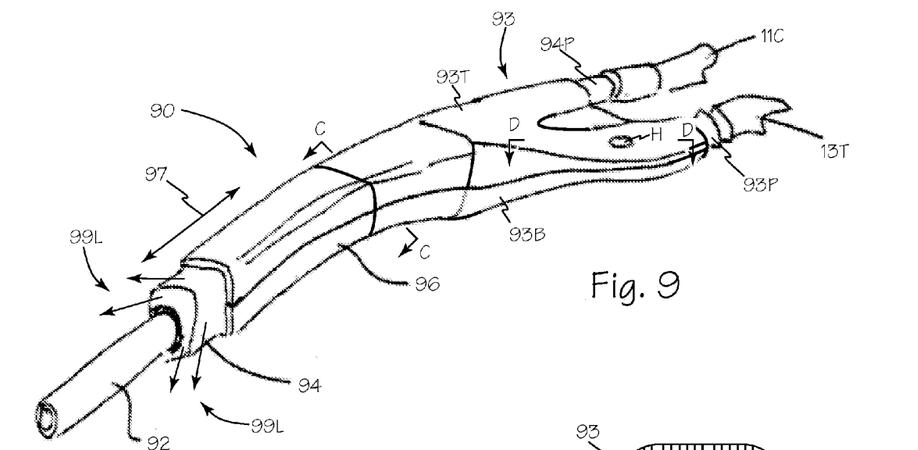
FIG. 9 is a perspective view of an illuminated suction apparatus with a handle.
Figure 10:
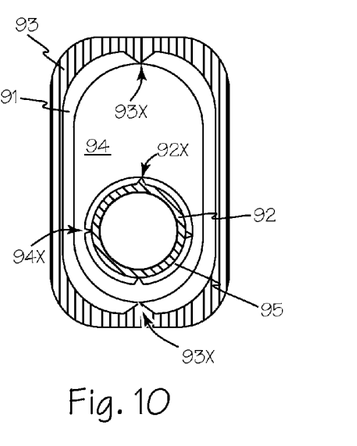
FIG. 10 is a cross section view of the illuminated suction apparatus of FIG. 8 taken along C-C.

Referring now to FIGS. 9 and 10, handle 93 of illuminated suction device 90 can be used to preserve TIR within illumination waveguide 94 through creation of air gap 91 (n=1.0) around waveguide 94. The design of the handle structure could include a portion that partially or fully covers the length of waveguide 94 to create the desired air gap. Features such as standoffs 93X can be molded into the surface of the handle in contact with the illuminator to create a gap between components. A similar configuration may be formed between suction tube 92 and illuminated waveguide 94, air gap 95 can be formed without standoffs based on the design tolerance between the ID of the illuminator and OD of the suction tube or with one or more standoffs such as standoff 92X or standoff 94X or any suitable combination.

The light output from illuminated waveguide 94 can be dynamically focused by permitting all or a portion of distal casing 96 to slide along axis 97 over the illuminator. The user can slide the tube down over the illuminated waveguide 94 to reduce the divergence angle and "focus" light 99L.

Figure 11:
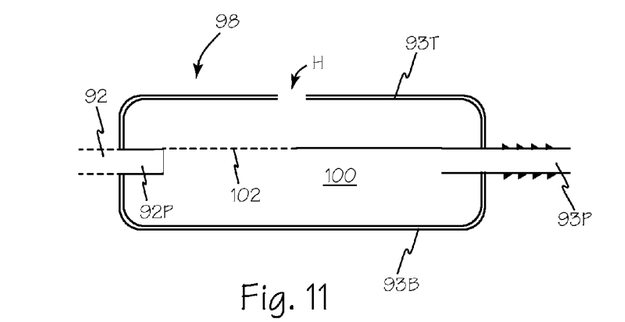
FIG. 11 is a cross section view of the handle of the illuminated suction apparatus of FIG. 10 taken along D-D.

Referring now to FIG. 11, the design of handle 93 must accommodate a suitable routing and termination of the suction channel and solid-state illuminator such that a suction flow control hole H is presented to the user in an ergonomically favorable position. Based on the way a user is expected to hold and manipulate an illuminated suction apparatus and the flow pattern of evacuated material from the patient, hole H may be present at or near the top surface 98 of the proximal handle. This can accomplished by forming handle 93 with at least two parts such as top section 93T and bottom section 93B. In addition to providing a shield for and proximal terminus for the illuminated waveguide 94, top handle portion 93T also contains suction flow control hole H. The top and bottom handle portions are sealed, with the bottom portion 93B creating a chamber in communication with proximal termination 92P of suction tube 92. Evacuated debris can be kept from flowing through to vacuum tube conduit 93P and out of hole H based on the geometry of the chamber 100 and pathway to flow control hole H. Alternatively a "strainer" or "filter" such as filter 102 may be included in handle 93 to capture any solid or liquid debris and prevent the debris from making their way out through hole H. Features in handle 93 could also allow the user to disassemble the top and bottom portions to clear any collected debris.

While the concepts presented thus far focus on a completely disposable non-modular device, alternative architectures are possible including the following:
  a. Disposable suction tips (varying French sizes & styles such as yankaeur, etc.) that integrate with a disposable device through a "quick-connect" attach & detach scheme.
  b. Disposable illumination sheaths such as waveguide sheath 16 may accommodate any suitable surgical instrument such as for example, a drill, burr or endoscope 18 which is encased, enclosed or otherwise surrounded by optical waveguide sheath 16. Illumination sheaths can be various materials such as flexible silicone.
  c. Disposable distal suction tips or other implements (nerve probes, etc) can also be integrated with a reusable proximal illuminator containing a traditional fiber optic bundle. This would enable rapid tip style exchange without the need to unplug cables. This approach also provides a means of unclogging trapped evacuated material.

d. Reusable proximal handles with removable single use illuminators/suction tubes. Enables easy change-out of devices without need to unplug cables.

Figure 12:
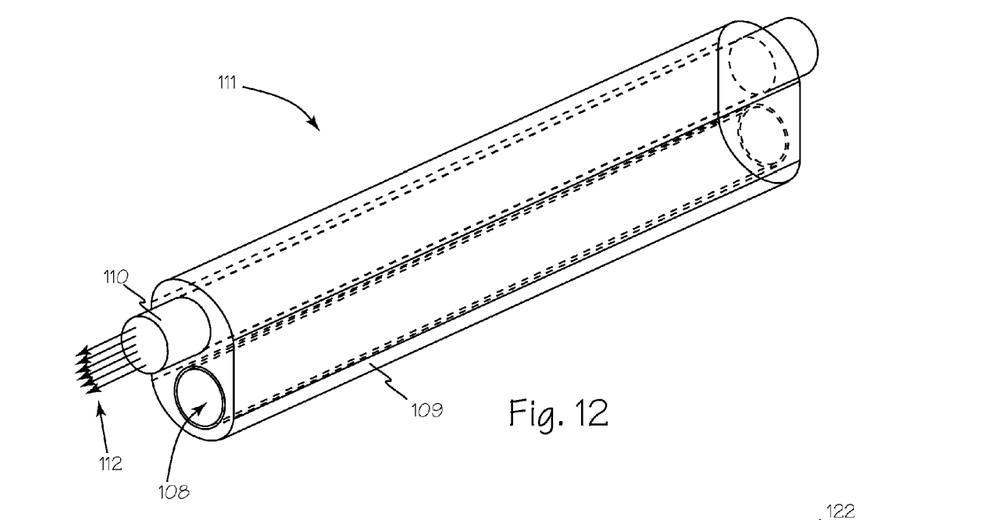
FIG. 12 is a perspective view of an alternate illuminated suction apparatus.

Referring now to FIG. 12, suction lumen 108 may be formed in suction element 109 that may be formed around an illuminator such as waveguide 110, as shown in illuminated suction apparatus 111. This configuration would allow for output light 112 to exit from a cylindrical source such as waveguide 110 without the shadowing caused by having a central illumination tube coaxial to the illuminator.

The routing of the suction conduit through the illuminator can be varied to optimize the illumination output and balance ergonomic considerations.

Figure 13:
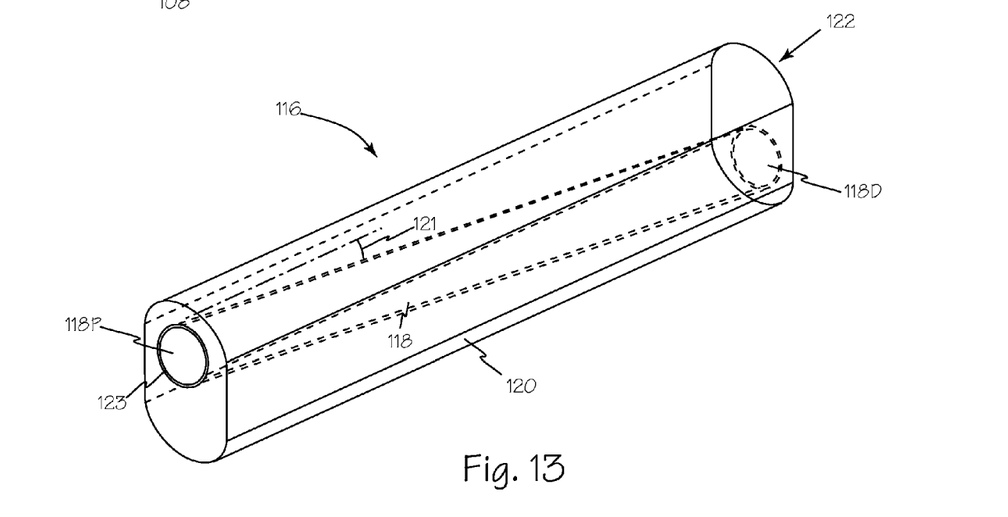
FIG. 13 is a perspective view of another alternate illuminated suction apparatus.

Referring now to FIG. 13, illuminated suction apparatus 116 is configured to enable suction tube 118 to be strategically routed through illumination waveguide 120 at angle 121 such that (1) proximal exposed end 118P is at the top of the device where the suction control function can be more readily accessed by the user (2) distal end 118D of the suction tube emerges from the bottom of the device below illumination output 122, providing optimized lighting of the surgical site from above the suction tube. In this configuration the suction tube changes light transmission paths through the illumination waveguide by introducing reflective surfaces which more thoroughly mix the light. It is possible to maintain the efficiency by using high reflective coatings, air gaps and cladding such as cladding 123. However, the added reflectance surfaces of the suction tube may cause the NA to increase.

Rotationally symmetric illuminated suction devices such as illuminated suction apparatus 116 may produce circumferential, uniform light output with strategic positioning of the suction tube that mitigates shadowing from the suction tube protruding from the distal surface of the waveguide. Light traversing the illuminated waveguide may have challenges with secondary reflectance surfaces, thus widening the light output pattern. Illuminated suction apparatus 116 is also expected to have a very large NA.

Illumination waveguides such as waveguides 14, 51, 70, 94, 110 and 120 may also be made malleable out of material like silicone. This can be useful to "pull over" an instrument like suction tube 12. The illumination waveguide can be made of a malleable material such as silicone allowing it to be pulled over a rigid suction tube, potentially lowering cost. Alternatively the malleable illumination waveguide material can be formed over a deformable suction tube structure, or a deformable structure that contains selective strength members (beams, etc). This would enable dynamic shaping of the suction tube to various desired shapes suited to the clinical application.

The illumination waveguide can be fabricated with materials of varying indices in a "stacked" or "composite" structure to shape and control the light output.

An alternative approach involves splitting an illumination waveguide with a solid light input with a circular or elliptical cross-section, routing and re-combining the waveguide into the original starting geometry. An illumination waveguide can then be molded over an internal suction tube. Alternatively, the suction tube in this configuration could run alongside the spit illuminator geometry.

If the cross section area is maintained (that is, distal and proximal ends on either side of split have same cross section, the intermediate shape of the waveguide can be manipulated. In the configuration listed above, there should be no significant loss of efficiency or change in NA. Thus, the input and output light patterns should be very similar in shape and intensity.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. An illuminated surgical device, said device comprising:
a tube having a proximal portion and a distal portion, and an inner surface and an outer surface;
first optical cladding at least partially circumferentially disposed around the outer surface of the tube; and
a crescent-shaped non-fiber optic optical waveguide having a proximal portion, a distal portion, a cross-sectional area, and an outer peripheral surface, a first portion of the outer peripheral surface having a convex shape and a second portion of the outer peripheral surface having a concave shape, wherein the second portion of the outer peripheral surface is disposed at least partially circumferentially around the tube such that the first optical cladding is disposed therebetween;
wherein light is transmitted through the optical waveguide by total internal reflection;
wherein the first optical cladding preserves total internal reflection in the optical waveguide; and
wherein the optical waveguide at least partially circumferentially illuminates around the tube.

2. The illuminated device of claim 1, wherein the cross-sectional area of the optical waveguide changes from the proximal portion of the waveguide to the distal portion thereof.

3. The illuminated device of claim 1, wherein the first optical cladding comprises fluorinated ethylene propylene.

4. The illuminated device of claim 1, wherein the first optical cladding comprises heat shrink material.

5. The illuminated device of claim 1, the first optical cladding comprises a coating.

6. The illuminated device of claim 1, wherein the optical waveguide is fabricated from cyclo olefin polymer or cyclo olefin copolymer.

7. The illuminated device of claim 1, wherein the proximal portion of the tube is angled relative to the distal portion thereof.

8. The illuminated device of claim 1, wherein the optical waveguide at least partially circumferentially illuminates around the tube and wherein the illumination is off-center relative to the tube.

9. The illuminated device of claim 1, wherein the tube further comprises a handle coupled to the proximal portion thereof.

10. The illuminated device of claim 9, wherein the tube comprises a suction tube, and wherein the handle has a suction flow control hole.

11. The illuminated device of claim 9, wherein the handle is disposed over at least a portion of the optical waveguide, and wherein an air gap is maintained therebetween.

12. The illuminated device of claim 1, further comprising an illumination input formed into the proximal portion of the optical waveguide for conducting light from a light source to the optical waveguide.

13. The illuminated device of claim 1, further comprising one or more microstructures on the distal portion of the optical waveguide for directing the light to form a preselected illumination pattern.

14. The illuminated device of claim 1, further comprising one or more light extracting structures near the distal portion on the outer surface of the optical waveguide.

15. The illuminated device of claim 1, wherein the tube comprises a suction tube having a distal suction tip, and wherein light output from the optical waveguide emanates from a point on the optical waveguide that is proximal of the distal suction tip.

16. The illuminated device of claim 1, wherein the optical waveguide completely surrounds at least a portion of the tube.

17. The illuminated device of claim 1, wherein the tube comprises a suction tube, and wherein the proximal portion of the tube is adapted to be coupled with a vacuum source.

18. The illuminated device of claim 1, wherein the first optical cladding has an index of refraction in the range of 1.00 to 1.46.

19. The illuminated device of claim 1, wherein the surgical or medical device further comprises a handle coupled to the proximal portion thereof, the handle is disposed over at least a portion of the optical waveguide, and wherein an air gap is maintained therebetween.

20. The illuminated device of claim 19, wherein the handle comprises standoffs on a surface thereof, the standoffs in contact with the optical waveguide to create the air gap between the handle and the waveguide.

21. The illuminated device of claim 1, further comprising one or more light extracting structures near the distal portion on the outer surface of the optical waveguide.

22. The illuminated device of claim 1, wherein the first optical cladding has an index of refraction in the range of 1.00 to 1.46.

23. The illuminated surgical device of claim 1, wherein the tube has a longitudinal axis and said optical waveguide has a longitudinal axis, and said longitudinal axis of the tube is not collinear with said longitudinal axis of the waveguide.

24. The illuminated surgical device of claim 1, wherein the optical waveguide has an asymmetric shape.

25. The illuminated surgical device of claim 1, wherein the optical waveguide has two planar surfaces parallel to the longitudinal axis of the optical waveguide.

26. The illuminated surgical device of claim 1, wherein the optical waveguide is not coaxial with the tube.

27. The illuminated surgical device of claim 1, wherein the waveguide includes micropattern structures.

28. The illuminated surgical device of claim 27, wherein the micropattern structures are provided on the proximal end of the waveguide.

29. The illuminated surgical device of claim 27, wherein the micropattern structures comprise micro lenses.

30. An illuminated surgical device, said device comprising:

a surgical or medical device having an outer surface;
first optical cladding at least partially circumferentially disposed around the outer surface of the surgical or medical device; and
a crescent-shaped non-fiber optic optical waveguide having two planar portions and first and second optical transmitting portions, said first optical transmitting portion including a through hole within which the surgical or medical device and first optical cladding are at least partially received;
wherein light is transmitted through the optical waveguide by total internal reflection; and
wherein the optical waveguide at least partially circumferentially illuminates around the surgical or medical device.

31. The illuminated surgical device of claim 30, wherein said first and second optical transmitting portions have first and second cross-sectional areas, respectively, and said first cross sectional area is less than said second cross sectional area.

32. The illuminated surgical device of claim 30, wherein said surgical or medical device has a longitudinal axis and said optical waveguide has a longitudinal axis, and said longitudinal axis of the surgical or medical device is not collinear with said longitudinal axis of the waveguide.

33. The illuminated surgical device of claim 30, wherein at least a portion of an exterior surface of the optical waveguide is planar.

34. The illuminated surgical device of claim 30, wherein two portions of an exterior surface of the optical waveguide are planar and are parallel to a longitudinal axis of the optical waveguide.

35. The illuminated device of claim 30, wherein the cross-sectional area of the optical waveguide changes from the proximal portion of the optical waveguide to the distal portion thereof.

36. The illuminated device of claim 30, wherein the cross-sectional area increases from the proximal portion of the optical waveguide to the distal portion of the optical waveguide.

37. The illuminated device of claim 30, wherein the optical waveguide at least partially circumferentially illuminates around the surgical or medical device and wherein the illumination is off-center relative to the surgical or medical device.

38. The illuminated device of claim 30, further comprising one or more microstructures on the distal portion of the optical waveguide for directing the light to form a preselected illumination pattern.

39. The illuminated surgical device of claim 30, wherein the optical waveguide has an asymmetric shape.

40. The illuminated surgical device of claim 30, wherein the optical waveguide is not coaxial with the surgical or medical device.

* * * * *